United States Patent
Todeschini

(10) Patent No.: US 9,572,901 B2
(45) Date of Patent: Feb. 21, 2017

(54) DEVICE HAVING LIGHT SOURCE TO REDUCE SURFACE PATHOGENS

(71) Applicant: Hand Held Products, Inc., Fort Mill, SC (US)

(72) Inventor: Erik Todeschini, Camillus, NY (US)

(73) Assignee: Hand Held Products, Inc., Fort Mill, SC (US)

( * ) Notice: Subject to any disclaimer, the term of this patent is extended or adjusted under 35 U.S.C. 154(b) by 200 days.

(21) Appl. No.: 14/019,616

(22) Filed: Sep. 6, 2013

(65) Prior Publication Data

US 2015/0071819 A1    Mar. 12, 2015

(51) Int. Cl.
*H01J 37/20*    (2006.01)
*A61L 2/00*    (2006.01)
*A61L 2/10*    (2006.01)

(52) U.S. Cl.
CPC .......... *A61L 2/0047* (2013.01); *A61L 2/0052* (2013.01); *A61L 2/10* (2013.01); *A61L 2202/14* (2013.01)

(58) Field of Classification Search
CPC ........................................................ A61L 2/10
USPC ....................................... 422/24; 250/455.11
See application file for complete search history.

(56) References Cited

U.S. PATENT DOCUMENTS

| | | | |
|---|---|---|---|
| 6,262,886 B1 * | 7/2001 | DiFonzo et al. | ......... 361/679.34 |
| 6,832,725 B2 | 12/2004 | Gardiner et al. | |
| 7,128,266 B2 | 10/2006 | Zhu et al. | |
| 7,159,783 B2 | 1/2007 | Walczyk et al. | |
| 7,413,127 B2 | 8/2008 | Ehrhart et al. | |
| 7,726,575 B2 | 6/2010 | Wang et al. | |
| 8,294,969 B2 | 10/2012 | Plesko | |
| 8,317,105 B2 | 11/2012 | Kotlarsky et al. | |
| 8,322,622 B2 | 12/2012 | Liu | |
| 8,366,005 B2 | 2/2013 | Kotlarsky et al. | |
| 8,371,507 B2 | 2/2013 | Haggerty et al. | |
| 8,376,233 B2 | 2/2013 | Van Horn et al. | |
| 8,381,979 B2 | 2/2013 | Franz | |
| 8,390,909 B2 | 3/2013 | Plesko | |
| 8,408,464 B2 | 4/2013 | Zhu et al. | |
| 8,408,468 B2 | 4/2013 | Horn et al. | |
| 8,408,469 B2 | 4/2013 | Good | |
| 8,424,768 B2 | 4/2013 | Rueblinger et al. | |
| 8,431,910 B1 * | 4/2013 | Perry | ...................... 250/455.11 |

(Continued)

FOREIGN PATENT DOCUMENTS

| | | |
|---|---|---|
| WO | 2013163789 A1 | 11/2013 |
| WO | 2013173985 A1 | 11/2013 |
| WO | 2014019130 A1 | 2/2014 |

OTHER PUBLICATIONS

U.S. Appl. No. 14/274,858 for Mobile Printer With Optional Battery Accessory, filed May 12, 2014, (Marty et al.), 26 pages.

(Continued)

*Primary Examiner* — Kevin Joyner
(74) *Attorney, Agent, or Firm* — Additon, Higgins & Pendleton, P.A.

(57) ABSTRACT

A self-disinfecting device includes a housing with translucent material and an internal light source that is used to reduce surface pathogens on the translucent material. The device includes a processor and a light source positioned within the housing. At least a portion of the housing is translucent to radiation, and the light source emits radiation at a wavelength and an intensity that kills pathogens residing on the outer surface of the housing.

20 Claims, 3 Drawing Sheets

(56) References Cited

U.S. PATENT DOCUMENTS

| | | | |
|---|---|---|---|
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 2007/0063048 A1 | 3/2007 | Havens et al. |
| 2008/0185432 A1 | 8/2008 | Caballero et al. |
| 2009/0134221 A1 | 5/2009 | Zhu et al. |
| 2009/0200378 A1* | 8/2009 | Doherty et al. ......... 235/462.01 |
| 2010/0104470 A1* | 4/2010 | McCabe ................ G05D 25/00 422/22 |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2011/0169999 A1 | 7/2011 | Grunow et al. |
| 2011/0202554 A1 | 8/2011 | Powilleit et al. |
| 2012/0111946 A1 | 5/2012 | Golant |
| 2012/0138685 A1 | 6/2012 | Qu et al. |
| 2012/0168511 A1 | 7/2012 | Kotlarsky et al. |
| 2012/0168512 A1 | 7/2012 | Kotlarsky et al. |
| 2012/0193407 A1 | 8/2012 | Barten |
| 2012/0193423 A1 | 8/2012 | Samek |
| 2012/0203647 A1 | 8/2012 | Smith |
| 2012/0223141 A1 | 9/2012 | Good et al. |
| 2012/0228382 A1 | 9/2012 | Havens et al. |
| 2012/0248188 A1 | 10/2012 | Kearney |
| 2013/0043312 A1 | 2/2013 | Van Horn |
| 2013/0045132 A1* | 2/2013 | Tumanov ....................... 422/24 |
| 2013/0056285 A1 | 3/2013 | Meagher |
| 2013/0070322 A1 | 3/2013 | Fritz et al. |
| 2013/0075168 A1 | 3/2013 | Amundsen et al. |
| 2013/0082104 A1 | 4/2013 | Kearney et al. |
| 2013/0175341 A1 | 7/2013 | Kearney et al. |
| 2013/0175343 A1 | 7/2013 | Good |
| 2013/0200158 A1 | 8/2013 | Feng et al. |
| 2013/0214048 A1 | 8/2013 | Wilz |
| 2013/0256418 A1 | 10/2013 | Havens et al. |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0278425 A1 | 10/2013 | Cunningham et al. |
| 2013/0287258 A1 | 10/2013 | Kearney |
| 2013/0292474 A1 | 11/2013 | Xian et al. |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0306728 A1 | 11/2013 | Thuries et al. |
| 2013/0306730 A1 | 11/2013 | Brady et al. |
| 2013/0306731 A1 | 11/2013 | Pedraro |
| 2013/0306734 A1 | 11/2013 | Xian et al. |
| 2013/0307964 A1 | 11/2013 | Bremer et al. |
| 2013/0308625 A1 | 11/2013 | Corcoran |
| 2013/0313324 A1 | 11/2013 | Koziol et al. |
| 2013/0313325 A1 | 11/2013 | Wilz et al. |
| 2013/0313326 A1 | 11/2013 | Ehrhart |
| 2013/0327834 A1 | 12/2013 | Hennick et al. |
| 2013/0341399 A1 | 12/2013 | Xian et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008430 A1 | 1/2014 | Soule et al. |
| 2014/0008439 A1 | 1/2014 | Wang |
| 2014/0021256 A1 | 1/2014 | Qu et al. |
| 2014/0025584 A1 | 1/2014 | Liu et al. |
| 2014/0027518 A1 | 1/2014 | Edmonds et al. |
| 2014/0034723 A1 | 2/2014 | Van Horn et al. |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061305 A1 | 3/2014 | Nahill et al. |
| 2014/0061306 A1 | 3/2014 | Wu et al. |
| 2014/0061307 A1 | 3/2014 | Wang et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |

(56) References Cited

U.S. PATENT DOCUMENTS

| | | | |
|---|---|---|---|
| 2014/0071840 A1 | 3/2014 | Venancio |
| 2014/0074746 A1 | 3/2014 | Wang |
| 2014/0075846 A1 | 3/2014 | Woodburn |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0084068 A1 | 3/2014 | Gillet et al. |
| 2014/0086348 A1 | 3/2014 | Peake et al. |
| 2014/0097249 A1 | 4/2014 | Gomez et al. |
| 2014/0098284 A1 | 4/2014 | Oberpriller et al. |
| 2014/0098792 A1 | 4/2014 | Wang et al. |
| 2014/0100774 A1 | 4/2014 | Showering |
| 2014/0100813 A1 | 4/2014 | Showering |
| 2014/0103115 A1 | 4/2014 | Meier et al. |
| 2014/0103416 A1 | 4/2014 | Ma et al. |
| 2014/0104413 A1 | 4/2014 | McCloskey et al. |
| 2014/0104414 A1 | 4/2014 | McCloskey et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131445 A1 | 5/2014 | Ding et al. |
| 2014/0133379 A1 | 5/2014 | Wang et al. |
| 2014/0140585 A1 | 5/2014 | Wang |
| 2014/0151453 A1 | 6/2014 | Meier et al. |
| 2014/0160329 A1 | 6/2014 | Ren et al. |

OTHER PUBLICATIONS

U.S. Appl. No. 14/264,173 for Autofocus Lens System for Indicia Readers filed Apr. 29, 2014, (Ackley et al.), 39 pages.
U.S. Appl. No. 14/230,322 for Focus Module and Components with Actuator filed Mar. 31, 2014 (Feng et al.); 92 pages.
U.S. Appl. No. 14/222,994 for Method and Apparatus for Reading Optical Indicia Using a Plurality of Data filed Mar. 24, 2014 (Smith et al.); 30 pages.
U.S. Appl. No. 14/231,898 for Hand-Mounted Indicia-Reading Device with Finger Motion Triggering filed Apr. 1, 2014 (Van Horn et al.); 36 pages.
U.S. Appl. No. 29/486,759 for an Imaging Terminal, filed Apr. 2, 2014 (Oberpriller et al.); 8 pages.
U.S. Appl. No. 29/436,337 for an Electronic Device, filed Nov. 5, 2012 (Fitch et al.); 19 pages.
U.S. Appl. No. 29/458,405 for an Electronic Device, filed Jun. 19, 2013 (Fitch et al.); 22 pages.
U.S. Appl. No. 29/459,620 for an Electronic Device Enclosure, filed Jul. 2, 2013 (London et al.); 21 pages.
U.S. Appl. No. 29/459,681 for an Electronic Device Enclosure, filed Jul. 2, 2013 (Chaney et al.); 14 pages.
U.S. Appl. No. 29/459,785 for a Scanner and Charging Base, filed Jul. 3, 2013 (Fitch et al.); 21 pages.
U.S. Appl. No. 29/459,823 for a Scanner, filed Jul. 3, 2013 (Zhou et al.); 13 pages.
U.S. Appl. No. 29/468,118 for an Electronic Device Case, filed Sep. 26, 2013 (Oberpriller et al.); 44 pages.
Dillow, Clay; "New Bacteria-Killing Light Can Destroy Superbugs With the Flip of a Switch", Nov. 15, 2010, [http://www.popsci.com/science/article/2010-11/researchers-use-bacteria-killing-light-destroy-pathogens-flip-switch], 2 pages.
U.S. Appl. No. 13/367,978, filed Feb. 7, 2012, (Feng et al.); now abandoned.
U.S. Appl. No. 13/736,139 for an Electronic Device Enclosure, filed Jan. 8, 2013 (Chaney); 40 pages.
U.S. Appl. No. 13/771,508 for an Optical Redirection Adapter, filed Feb. 20, 2013 (Anderson); 26 pages.
U.S. Appl. No. 13/780,356 for a Mobile Device Having Object Identification Interface, filed Feb. 28, 2013 (Samek et al.); 21 pages.
U.S. Appl. No. 13/852,097 for a System and Method for Capturing and Preserving Vehicle Event Data, filed Mar. 28, 2013 (Barker et al.); 20 pages.
U.S. Appl. No. 13/902,110 for a System and Method for Display of Information Using a Vehicle-Mount Computer, filed May 24, 2013 (Hollifield); 29 pages.
U.S. Appl. No. 13/902,144, for a System and Method for Display of Information Using a Vehicle-Mount Computer, filed May 24, 2013 (Chamberlin); 23 pages.
U.S. Appl. No. 13/902,242 for a System For Providing A Continuous Communication Link With A Symbol Reading Device, filed May 24, 2013 (Smith et al.); 24 pages.
U.S. Appl. No. 13/912,262 for a Method of Error Correction for 3D Imaging Device, filed Jun. 7, 2013 (Jovanovski et al.); 33 pages.
U.S. Appl. No. 13/912,702 for a System and Method for Reading Code Symbols at Long Range Using Source Power Control, filed Jun. 7, 2013 (Xian et al.); 24 pages.
U.S. Appl. No. 13/922,339 for a System and Method for Reading Code Symbols Using a Variable Field of View, filed Jun. 20, 2013 (Xian et al.); 23 pages.
U.S. Appl. No. 13/927,398 for a Code Symbol Reading System Having Adaptive Autofocus, filed Jun. 26, 2013 (Todeschini); 24 pages.
U.S. Appl. No. 13/930,913 for a Mobile Device Having an Improved User Interface for Reading Code Symbols, filed Jun. 28, 2013 (Gelay et al.); 24 pages.
U.S. Appl. No. 13/933,415 for an Electronic Device Case, filed Jul. 2, 2013 (London et al.); 47 pages.
U.S. Appl. No. 13/947,296 for a System and Method for Selectively Reading Code Symbols, filed Jul. 22, 2013 (Rueblinger et al.); 29 pages.
U.S. Appl. No. 13/950,544 for a Code Symbol Reading System Having Adjustable Object Detection, filed Jul. 25, 2013 (Jiang); 28 pages.
U.S. Appl. No. 13/961,408 for a Method for Manufacturing Laser Scanners, filed Aug. 7, 2013 (Saber et al.); 26 pages.
U.S. Appl. No. 14/018,729 for a Method for Operating a Laser Scanner, filed Sep. 5, 2013 (Feng et al.); 24 pages.
U.S. Appl. No. 14/019,616 for a Device Having Light Source to Reduce Surface Pathogens, filed Sep. 6, 2013 (Todeschini); 23 pages.
U.S. Appl. No. 14/023,762 for a Handheld Indicia Reader Having Locking Endcap, filed Sep. 11, 2013 (Gannon); 31 pages.
U.S. Appl. No. 14/035,474 for Augmented-Reality Signature Capture, filed Sep. 24, 2013 (Todeschini); 33 pages.
U.S. Appl. No. 14/047,896 for Terminal Having Illumination and Exposure Control filed Oct. 7, 2013 (Jovanovski et al.); 32 pages.
U.S. Appl. No. 14/053,175 for Imaging Apparatus Having Imaging Assembly, filed Oct. 14, 2013 (Barber); 39 pages.
U.S. Appl. No. 14/055,234 for Dimensioning System, filed Oct. 16, 2013 (Fletcher); 26 pages.
U.S. Appl. No. 14/053,314 for Indicia Reader, filed Oct. 14, 2013 (Huck); 29 pages.
U.S. Appl. No. 14/065,768 for Hybrid System and Method for Reading Indicia, filed Oct. 29, 2013 (Meier et al.); 22 pages.
U.S. Appl. No. 14/074,746 for Self-Checkout Shopping System, filed Nov. 8, 2013 (Hejl et al.); 26 pages.
U.S. Appl. No. 14/074,787 for Method and System for Configuring Mobile Devices via NFC Technology, filed Nov. 8, 2013 (Smith et al.); 28 pages.
U.S. Appl. No. 14/087,190 for Optimal Range Indicators for Bar Code Validation, filed Nov. 22, 2013 (Hejl); 27 pages.
U.S. Appl. No. 14/345,735 for Optical Indicia Reading Terminal with Combined Illumination filed Mar. 19, 2014 (Ouyang); 19 pages.

(56) References Cited

OTHER PUBLICATIONS

U.S. Appl. No. 14/101,965 for High Dynamic-Range Indicia Reading System, filed Dec. 10, 2013 (Xian); 28 pages.
U.S. Appl. No. 14/118,400 for Indicia Decoding Device with Security Lock, filed Nov. 18, 2013 (Liu); 28 pages.
U.S. Appl. No. 14/150,393 for Incicia-reader Having Unitary Construction Scanner, filed Jan. 8, 2014 (Colavito et al.); 28 pages.
U.S. Appl. No. 14/154,207 for Laser Barcode Scanner, filed Jan. 14, 2014 (Hou et al.); 26 pages.
U.S. Appl. No. 14/154,915 for Laser Scanning Module Employing a Laser Scanning Assembly having Elastomeric Wheel Hinges, filed Jan. 14, 2014 (Havens et al.); 24 pages.
U.S. Appl. No. 14/158,126 for Methods and Apparatus to Change a Feature Set on Data Collection Devices, filed Jan. 17, 2014 (Berthiaume et al.); 53 pages.
U.S. Appl. No. 14/342,551 for Terminal Having Image Data Format Conversion filed Mar. 4, 2014 (Lui et al.); 25 pages.
U.S. Appl. No. 14/342,544 for Imaging Based Barcode Scanner Engine with Multiple Elements Supported on a Common Printed Circuit Board filed Mar. 4, 2014 (Liu et al.); 27 pages.
U.S. Appl. No. 14/257,174 for Reading Apparatus Having Partial Frame Operating Mode filed Apr. 21, 2014, (Barber et al.), 67 pages.
U.S. Appl. No. 14/200,405 for Indicia Reader for Size-Limited Applications filed Mar. 7, 2014 (Feng et al.); 42 pages.
U.S. Appl. No. 14/166,103 for Indicia Reading Terminal Including Optical Filter filed Jan. 28, 2014 (Lu et al.); 29 pages.

\* cited by examiner

DEVICE HAVING LIGHT SOURCE TO REDUCE SURFACE PATHOGENS

FIELD OF THE INVENTION

The present invention relates to the field of decontamination and, more specifically, to a self-disinfecting device.

BACKGROUND

Many products are used in environments where bacteria reduction or disinfection is mission critical. As an example, products such as hand-held mobile computers and bar code scanners are used regularly in hospitals, where decontamination is critically important.

In the hospital environment, hand-held mobile computers and bar code scanners are carried room-to-room by doctors and nurses in the performance of their duties. Because these devices may be regularly used or carried by doctors, nurses, or other hospital staff throughout the hospital environment, these devices acquire and carry with them contaminants and pathogens, such as bacteria.

As devices such as hand-held mobile computers and bar code scanners are carried throughout the hospital environment and from room to room, patients can be exposed to contaminants (e.g., bacteria) that are carried by the devices posing serious health risks. Because of the risk to patients and visitors, as well as to hospital employees, hospital staff are required to frequently clean these kinds of devices.

While traditional methods of cleansing, such as the application and use of cleaning solutions, is a somewhat effective method of reducing bacteria or other contaminants, the effectiveness of such traditional methods of disinfection is completely dependent upon the quality and thoroughness of the cleaning job that is performed by each employee that is tasked with cleaning the devices.

Therefore, a need exists for more efficient and effective methods and devices for disinfecting products, including but not limited to hand-held mobile computers and bar code scanners.

SUMMARY

Accordingly, in one aspect, the present invention embraces self-disinfecting devices including a housing that has translucent material through which light (e.g., electromagnetic radiation) may pass, a light source positioned within the housing, and an electrical power source for powering the light source. The light source illuminates the translucent material such that the light source disinfects the surface of the housing through which the light passes.

In another exemplary embodiment, the self-disinfecting device includes a power source for powering the device's light source.

In yet another exemplary embodiment, the power source for the self-disinfecting device is an electrical power source.

In yet another exemplary embodiment, the self-disinfecting device includes a reflector that directs light produced by the light source to the housing's translucent material.

In yet another exemplary embodiment, the self-disinfecting device includes a lens to direct light produced by the device's light source to the housing's translucent material.

In yet another exemplary embodiment, the self-disinfecting device's light source(s) emits light at a wavelength and an intensity that kills bacteria without substantially harming human skin.

In yet another exemplary embodiment, the housing's translucent material is present in an area designed to be touched during operation of the device.

In yet another exemplary embodiment, the self-disinfecting device is a hand-held computer.

In yet another exemplary embodiment, the self-disinfecting device is a hand-held scanner.

In another aspect, the present invention embraces a hand-held device that is capable of self-disinfection. The hand-held device includes a processor and a housing that substantially encloses the processor. The housing is at least partially formed of a material that is translucent to light. The device also includes an ultraviolet light source positioned within the housing for emitting light at a wavelength and an intensity that kills bacteria on the outer surface of the housing's translucent material.

In another exemplary embodiment, the hand-held device includes a power source for powering the ultraviolet light source.

In yet another exemplary embodiment, the power source for the hand-held device is an electrical power source.

In yet another exemplary embodiment, the ultraviolet light source of the hand-held device is a light-emitting diode.

In yet another exemplary embodiment, the ultraviolet light source of the hand-held device is a plurality of light-emitting diodes arranged in an array.

In yet another exemplary embodiment, the ultraviolet light is guided to the outer surface of the housing's translucent material.

In yet another exemplary embodiment, the ultraviolet light is guided through glass to the outer surface of the housing's translucent material.

In yet another exemplary embodiment, the housing includes a handle formed of material that is translucent to ultraviolet light.

In yet another exemplary embodiment, the device is a hand-held computer.

In yet another exemplary embodiment, the device is a hand-held scanner.

In another aspect, the present invention embraces a method for disinfecting a device. The method includes providing a device that includes a processor and a light source positioned within a housing. At least a portion of the housing is translucent to radiation. The method further includes emitting radiation from the light source at a wavelength and an intensity that kills bacteria on the outer surface of the housing.

The foregoing illustrative summary, as well as other exemplary objectives and/or advantages of the invention, and the manner in which the same are accomplished, are further explained within the following detailed description and its accompanying drawings.

DETAILED DESCRIPTION

The present invention embraces self-disinfecting devices and related methods for disinfecting devices. In particular, the present invention embraces self-disinfecting devices having a housing with translucent material and an internal and/or external light source that is used to reduce surface bacteria on the translucent material. Although surface bacteria are the contaminant commonly referred to herein, this term is used in a general sense and can include any other disease causing organism or pathogen.

Non-limiting examples of typical self-disinfecting devices may include hand-held computers, hand-held scanners, and similar products that may be used in any environment where reduction of contaminants is advantageous (e.g., a hospital environment). References herein to particular kinds of devices or device environments are not intended to limit the disclosure to particular devices, and those having ordinary skill in the art will recognize that a number of products for which elimination of surface pathogens would be beneficial could be employed.

Figure 1:
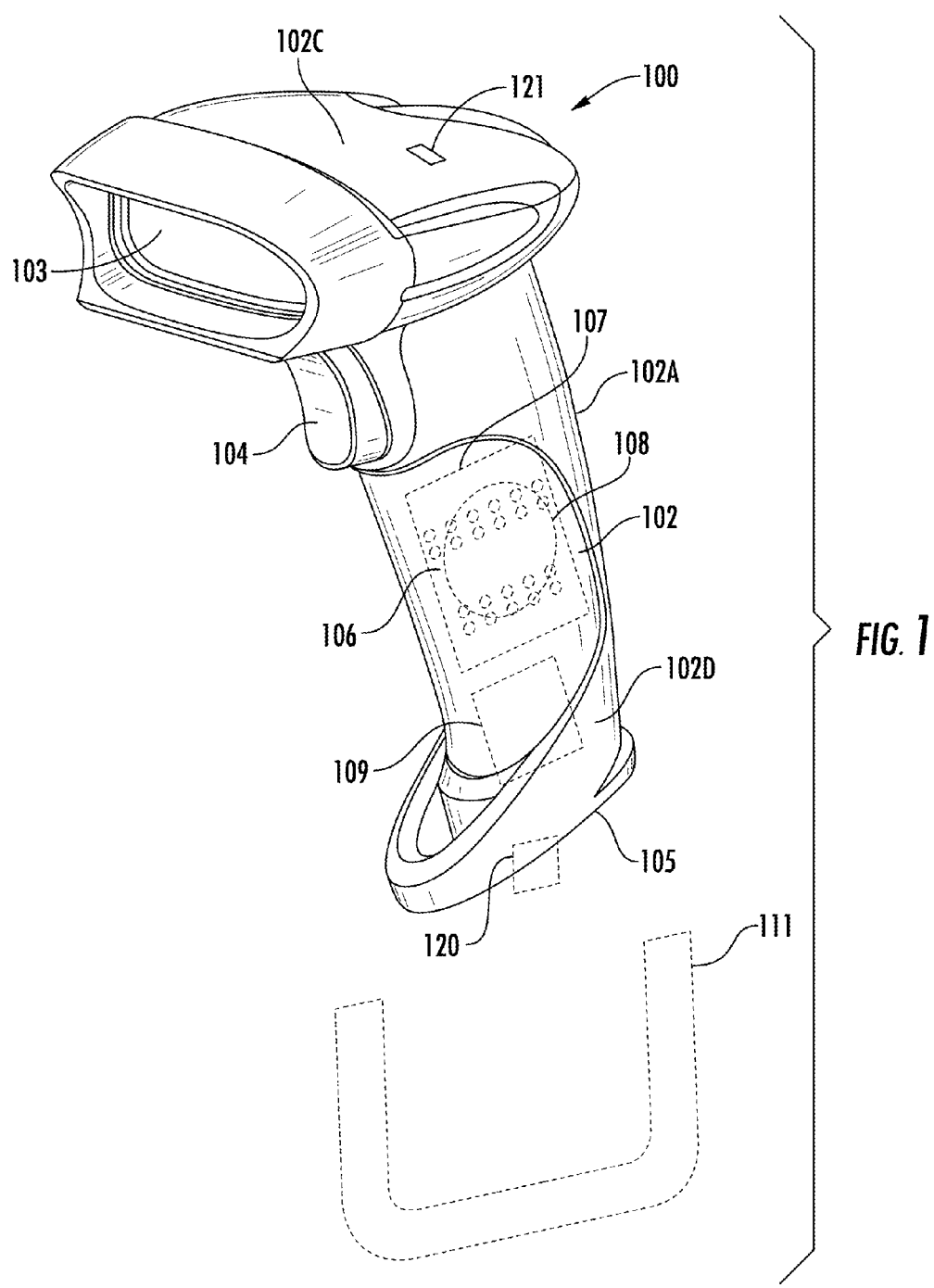
FIG. 1 depicts an exemplary self-disinfecting device and illustrates certain components for an exemplary self-disinfecting device according to the present invention.

Referring now to the drawings, FIG. 1 depicts an exemplary self-disinfecting device according to the present invention, specifically a self-disinfecting hand-held scanner (100). The exemplary self-disinfecting hand-held scanner (100) includes a hand-supportable housing (102) incorporating translucent material (102A). The translucent material (102A) may include any material that at least partially allows ultraviolet radiation to pass through to the outer surface of the translucent material (102A) at a wavelength and intensity necessary to disinfect the surface of the translucent material (102A) (e.g., plastic, glass, acrylic, resin or any other translucent material that could be used for a product housing). The translucent material (102A) may be of a kind and configuration known within the art that will not substantially degrade upon repeated or prolonged exposure to ultraviolet radiation.

As depicted in FIG. 1, the exemplary hand-held scanner's (100) housing (102) has a head portion (102C) that is provided with a light transmission window (103) integrated within the head portion of the housing (102). The light transmission window (103) may include a laser (e.g., infrared) or an image reading sensor that is utilized for reading symbols, images, and the like. As illustrated in FIG. 1, a manually actuated trigger switch (104) may be depressed to activate the scanning module.

The base structure (102D) of the hand-held scanner's housing (102) may include a charging mechanism (105) for providing electrical power from a charging base (111) to an electrical power source (109), such as an internal battery positioned within the housing (102). Alternatively, those having skill in the art will recognize that other internal or external power sources may be utilized in order to provide power to the self-disinfecting hand-held scanner (100) of the exemplary embodiment.

An ultraviolet light source (106) is positioned within the housing (102). The ultraviolet light source (106) may include one or more light-emitting-diodes (LED) (e.g., two or more LEDs configured in an LED array) or may take any other form that is capable of providing ultraviolet radiation of a sufficient wavelength and intensity known within the art to decontaminate the surface of the translucent material (102A). Although ultraviolet light and light sources are typically referred to herein, these terms are used in a general sense and can include any other light source which can be utilized to decontaminate the surface of the translucent material (102A). For example, the light source (106) may alternatively utilize HINS (High Intensity, Narrow Spectrum) light to decontaminate the surface (102A).

Reflective material (107) and/or a lens (108) may be utilized for efficiently guiding ultraviolet light from the ultraviolet light source (106) to the translucent material (102A). The ultraviolet light source (106) may alternatively be guided to the surface via total internal reflection through a medium (e.g., glass, plastic, or acrylic). A manual switch (121) may be provided on the hand-held scanner's (100) housing (102) to manually start and stop the emission of ultraviolet light from the ultraviolet light source (106) (i.e., starting and stopping the cleaning mode of the self-disinfecting hand-supportable scanner (100)).

Although internal light source (106) is depicted in FIG. 1, an at least partially external light source (not depicted) may be utilized in addition to, or as an alternative to, internal light source (106) in order to disinfect the exemplary device (100). The external light source may be positioned on the head portion (102C) above the trigger (104) of the device (100) such that the external light source is capable of disinfecting the surface of the trigger (104) and the handle portion of the housing (102) when activated. Those having skill in the art will appreciate that the external light source may alternatively be located in the charging base (111) or in other locations such that the surface of the housing (102) will be disinfected when the external light source is activated.

Figure 2:
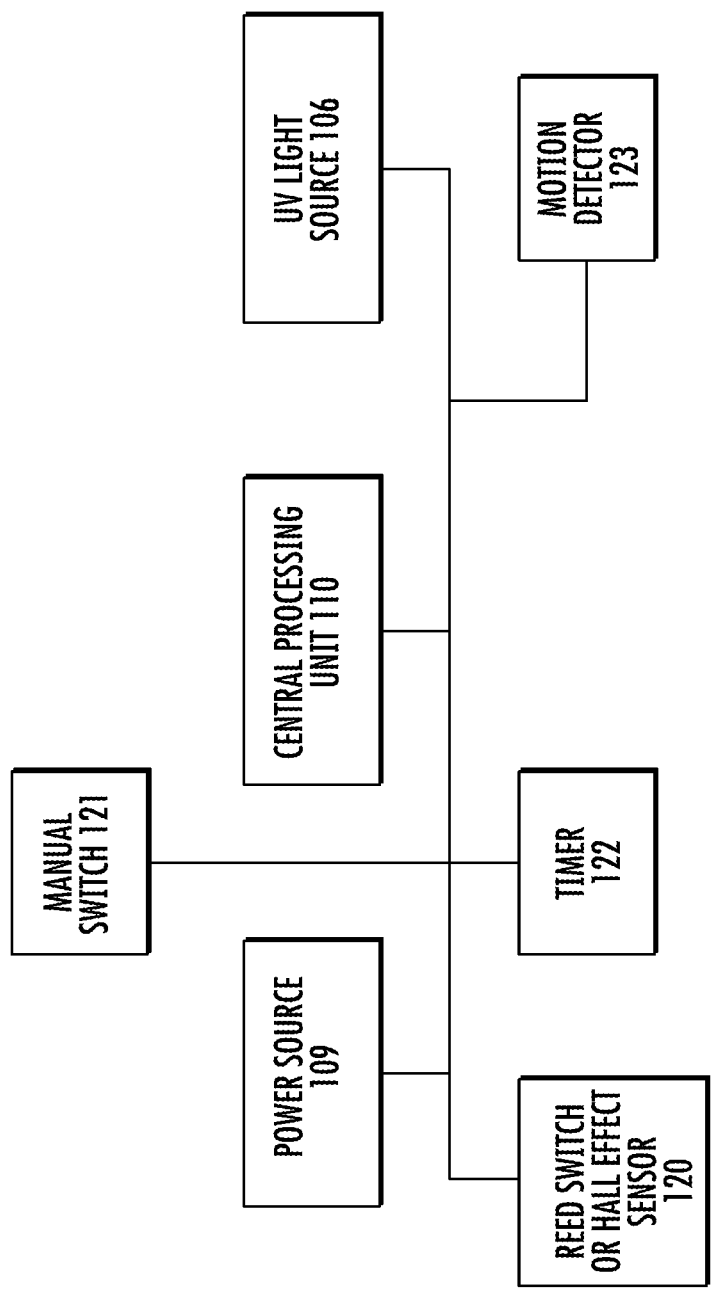
FIG. 2 illustrates via a schematic block diagram typical components for an exemplary self-disinfecting device according to the present invention.

In addition to, or in the place of, the operation of the manual switch (121), various cleaning cycles may be utilized to disinfect the exemplary device (100). In this regard, FIG. 2 is a schematic block diagram illustrating various components that may be utilized in order to implement alternative disinfecting cycles for the exemplary self-disinfecting device (100). These components may be controlled by a central processing unit (110), as well as by additional components of typical computer systems that are known in the art but are not depicted herein (e.g., a mass storage device for storing an operating system and application programs).

As depicted in FIG. 2, a timer (122) may be utilized for starting and stopping the cleaning mode at specified time periods sufficient to continually keep the device (100) at an effective level of disinfection for the environment in which it is being used. The timer may be set to disinfect the device during periods when the exemplary device (100) is not typically in use (e.g., when the device is resting in a charging base).

An exemplary self-disinfecting device (100) according to the present invention may also incorporate sensors (FIG. 2) to facilitate implementation of the disinfecting process, such as a reed switch or Hall-effect sensor (120) in the base structure (102D) and/or a motion sensor(s) (123) to detect movement of the device (100). The motion sensor (123) could be an accelerometer or some other device to sense motion that is known within the art. The motion sensor (123) could be used to prevent the discharge of ultraviolet light when the scanner (100) is being carried by a user or when the device is in use.

A Reed switch or Hall-effect sensor (120), which is positioned in the base structure (102D), may be utilized to allow the scanner (100) to enter cleaning mode when the device is on the charging base. In this regard, the device will not be carried or otherwise in use during operation of the cleaning mode. The charging base (111) could contain a magnet so that when sensor (120) was in proximity of the magnetic field, the ultraviolet "light wash" cycle would begin.

Alternatively, or in addition to implementation of the sensors (120, 123) set forth previously, light wavelengths that are not damaging to human skin may be used in connection with the cleaning cycle of the exemplary device (100). Methods of decontamination have been developed, for example, at the University of Glasgow, Scotland UK, which utilize a narrow spectrum of visible light wavelengths known as HINS (High Intensity, Narrow Spectrum) light. HINS light excites molecules within bacteria such that the bacteria produce a chemically lethal response. The HINS light, however, is not damaging to humans. To remedy concerns regarding user exposure to harmful ultraviolet radiation, this technology may also be implemented within the exemplary device (100) as a safety precaution.

Figure 3:
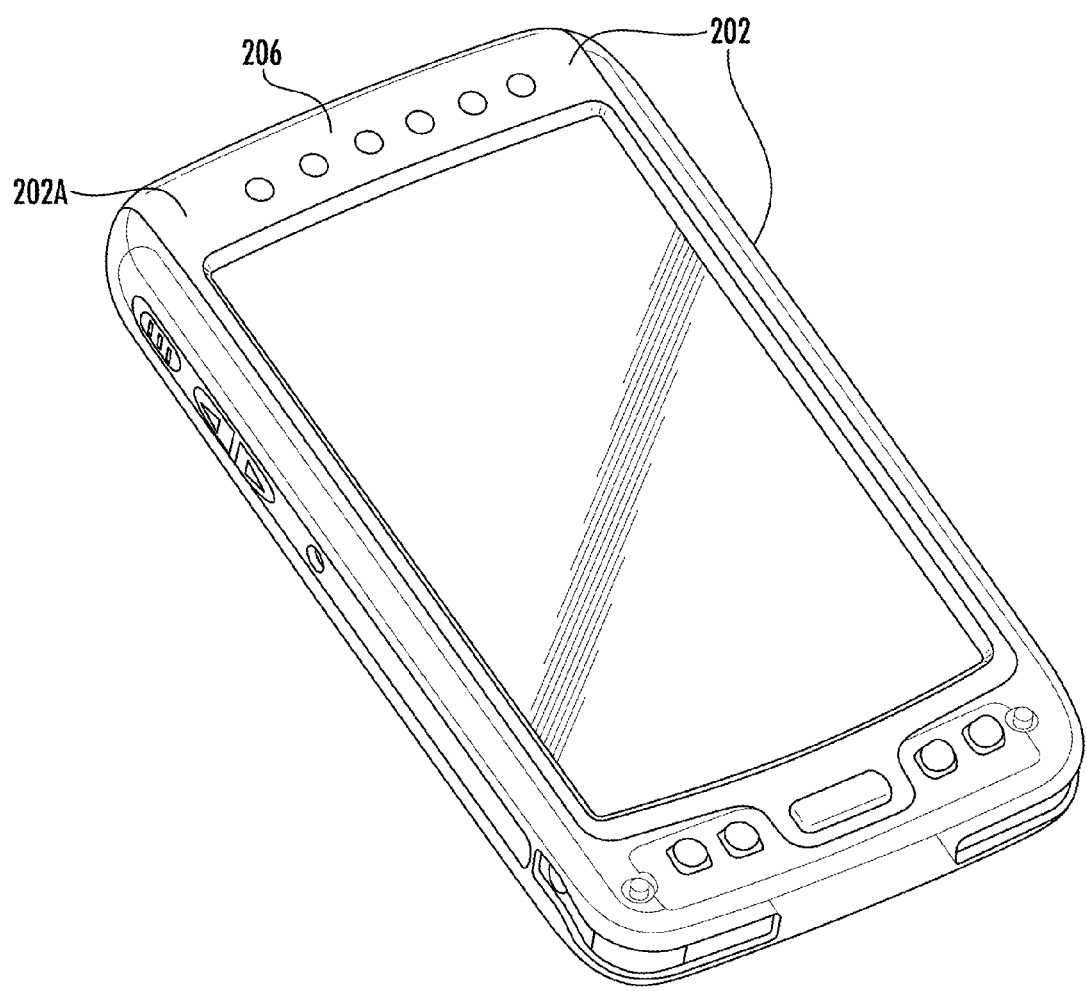
FIG. 3 depicts another exemplary self-disinfecting device and illustrates certain components for an exemplary self-disinfecting device according to the present invention.

FIG. 3 depicts an exemplary self-disinfecting hand-held computer (200) according to the present invention. The exemplary self-disinfecting hand-held computer (200) may include similar components as set forth relating to the exemplary self-disinfecting scanner (100) (FIGS. 1, 2), which are not repeated herein (FIG. 3).

As depicted (FIG. 3), the exemplary self-disinfecting hand-held computer (200) includes a hand-supportable housing (202) incorporating translucent material (202A). An ultraviolet light source (206), in this case a light-emitting-diode (LED) array, is positioned within the hand-supportable housing (202). When activated, the ultraviolet light source (206) provides ultraviolet radiation of a sufficient wavelength and intensity known within the art to decontaminate the surface of the translucent material (202A).

To supplement the present disclosure, this application incorporates entirely by reference the following patents, patent application publications, and patent applications: U.S. Pat. No. 6,832,725; U.S. Pat. No. 7,159,783; U.S. Pat. No. 7,128,266; U.S. Pat. No. 7,413,127; U.S. Pat. No. 7,726,575; U.S. Pat. No. 8,390,909; U.S. Pat. No. 8,294,969; U.S. Pat. No. 8,408,469; U.S. Pat. No. 8,408,468; U.S. Pat. No. 8,381,979; U.S. Pat. No. 8,408,464; U.S. Pat. No. 8,317,105; U.S. Pat. No. 8,366,005; U.S. Pat. No. 8,424,768; U.S. Pat. No. 8,322,622; U.S. Pat. No. 8,371,507; U.S. Pat. No. 8,376,233; U.S. Pat. No. 8,457,013; U.S. Pat. No. 8,448,863; U.S. Pat. No. 8,459,557; U.S. Pat. No. 8,469,272; U.S. Pat. No. 8,474,712; U.S. Pat. No. 8,479,992; U.S. Pat. No. 8,490,877; U.S. Pat. No. 8,517,271; U.S. Pat. No. 8,523,076; U.S. Pat. No. 8,528,819; U.S. Patent Application Publication No. 2012/0111946; U.S. Patent Application Publication No. 2012/0223141; U.S. Patent Application Publication No. 2012/0193423; U.S. Patent Application Publication No. 2012/0203647; U.S. Patent Application Publication No. 2012/0248188; U.S. Patent Application Publication No. 2012/0228382; U.S. Patent Application Publication No. 2012/0193407; U.S. Patent Application Publication No. 2012/0168511; U.S. Patent Application Publication No. 2012/0168512; U.S. Patent Application Publication No. 2010/0177749; U.S. Patent Application Publication No. 2010/0177080; U.S. Patent Application Publication No. 2010/0177707; U.S. Patent Application Publication No. 2010/0177076; U.S. Patent Application Publication No. 2009/0134221; U.S. Patent Application Publication No. 2012/0318869; U.S. Patent Application Publication No. 2013/0043312; U.S. Patent Application Publication No. 2013/0068840; U.S. Patent Application Publication No. 2013/0070322; U.S. Patent Application Publication No. 2013/0075168; U.S. Patent Application Publication No. 2013/0056285; U.S. Patent Application Publication No. 2013/0075464; U.S. Patent Application Publication No. 2013/0082104; U.S. Patent Application Publication No. 2010/0225757; U.S. Patent Application Publication No. 2013/0175343; U.S. patent application Ser. No. 13/347,193 for a HYBRID-TYPE BIOPTICAL LASER SCANNING AND DIGITAL IMAGING SYSTEM EMPLOYING DIGITAL IMAGER WITH FIELD OF VIEW OVERLAPPING FIELD OF FIELD OF LASER SCANNING SUBSYSTEM, filed Jan. 10, 2012 (Kearney et al.); U.S. patent application Ser. No. 13/367,047 for LASER SCANNING MODULES EMBODYING SILICONE SCAN ELEMENT WITH TORSIONAL HINGES, filed Feb. 6, 2012 (Feng et al.); U.S. patent application Ser. No. 13/400,748 for a LASER SCANNING BAR CODE SYMBOL READING SYSTEM HAVING INTELLIGENT SCAN SWEEP ANGLE ADJUSTMENT CAPABILITIES OVER THE WORKING RANGE OF THE SYSTEM FOR OPTIMIZED BAR CODE SYMBOL READING PERFORMANCE, filed Feb. 21, 2012 (Wilz); U.S. patent application Ser. No. 13/432,197 for a LASER SCANNING SYSTEM USING LASER BEAM SOURCES FOR PRODUCING LONG AND SHORT WAVELENGTHS IN COMBINATION WITH BEAM-WAIST EXTENDING OPTICS TO EXTEND THE DEPTH OF FIELD THEREOF WHILE RESOLVING HIGH RESOLUTION BAR CODE SYMBOLS HAVING MINIMUM CODE ELEMENT WIDTHS, filed Mar. 28, 2012 (Havens et al.); U.S. patent application Ser. No. 13/492,883 for a LASER SCANNING MODULE WITH ROTATABLY ADJUSTABLE LASER SCANNING ASSEMBLY, filed Jun. 10, 2012 (Hennick et al.); U.S. patent application Ser. No. 13/367,978 for a LASER SCANNING MODULE EMPLOYING AN ELASTOMERIC U-HINGE BASED LASER SCANNING ASSEMBLY, filed Feb. 7, 2012 (Feng et al.); U.S. patent application Ser. No. 13/852,097 for a System and Method for Capturing and Preserving Vehicle Event Data, filed Mar. 28, 2013 (Barker et al.); U.S. patent application Ser. No. 13/780,356 for a Mobile Device Having Object-Identification Interface, filed Feb. 28, 2013 (Samek et al.); U.S. patent application Ser. No. 13/780,158 for a Distraction Avoidance System, filed Feb. 28, 2013 (Sauerwein); U.S. patent application Ser. No. 13/784,933 for an Integrated Dimensioning and Weighing System, filed Mar. 5, 2013 (McCloskey et al.); U.S. patent application Ser. No. 13/785,177 for a Dimensioning System, filed Mar. 5, 2013 (McCloskey et al.); U.S. patent application Ser. No. 13/780,196 for Android Bound Service Camera Initialization, filed Feb. 28, 2013 (Todeschini et al.); U.S. patent application Ser. No. 13/792,322 for a Replaceable Connector, filed Mar. 11, 2013 (Skvoretz); U.S. patent application Ser. No. 13/780,271 for a Vehicle Computer System with Transparent Display, filed Feb. 28, 2013 (Fitch et al.); U.S. patent application Ser. No. 13/736,139 for an Electronic Device Enclosure, filed Jan. 8, 2013 (Chaney); U.S. patent application Ser. No. 13/771,508 for an Optical Redirection Adapter, filed Feb. 20, 2013 (Anderson); U.S. patent application Ser. No. 13/750,304 for Measuring Object Dimensions Using Mobile Computer, filed Jan. 25, 2013; U.S. patent application Ser. No. 13/471,973 for Terminals and Methods for Dimensioning Objects, filed May 15, 2012; U.S. patent application Ser. No. 13/895,846 for a Method of Programming a Symbol Reading System, filed Apr. 10, 2013 (Corcoran); U.S. patent application Ser. No. 13/867,386 for a Point of Sale (POS) Based Checkout System Supporting a Customer-Transparent Two-Factor Authentication Process During Product Checkout Operations, filed Apr. 22, 2013 (Cunningham et al.); U.S. patent application Ser. No. 13/888,884 for an Indicia Reading System Employing Digital Gain Control, filed May 7, 2013 (Xian et al.); U.S. patent application Ser. No. 13/895,616 for a Laser Scanning Code Symbol Reading System Employing Multi-Channel Scan Data Signal Processing with Synchronized Digital Gain Control (SDGC) for Full Range Scanning, filed May 16, 2013 (Xian et al.); U.S. patent application Ser. No. 13/897,512 for a Laser Scanning Code Symbol Reading System Providing Improved Control over the Length and Intensity Characteristics of a Laser Scan Line Projected Therefrom Using Laser Source Blanking Control, filed May 20, 2013 (Brady et al.); U.S. patent application Ser. No. 13/897,634 for a Laser Scanning Code Symbol Reading System Employing Programmable Decode Time-Window Filtering, filed May 20, 2013 (Wilz, Sr. et al.); U.S. patent application Ser. No. 13/902,242 for a System For Providing A Continuous Communication Link With A Symbol Reading Device, filed May 24, 2013 (Smith et al.); U.S. patent application Ser. No. 13/902,144, for a System and Method for Display of Information Using a Vehicle-Mount Computer, filed May 24, 2013 (Chamberlin); U.S. patent application Ser. No. 13/902,110 for a System and Method for Display of Information Using a Vehicle-Mount Computer, filed May 24, 2013 (Hollifield); U.S. patent application Ser. No. 13/912,262 for a Method of Error Correction for 3D Imaging Device, filed Jun. 7, 2013 (Jovanovski et al.); U.S. patent application Ser. No. 13/912,702 for a System and Method for Reading Code Symbols at Long Range Using Source Power Control, filed Jun. 7, 2013 (Xian et al.); U.S. patent application Ser. No. 13/922,339 for a System and Method for Reading Code Symbols Using a Variable Field of View, filed Jun. 20, 2013 (Xian et al.); U.S. patent application Ser. No. 13/927,398 for a Code Symbol Reading System Having Adaptive Autofocus, filed Jun. 26, 2013 (Todeschini); U.S. patent application Ser. No. 13/930,913 for a Mobile Device Having an Improved User Interface for Reading Code Symbols, filed Jun. 28, 2013 (Gelay et al.); U.S. patent application Ser. No. 13/933,415 for an Electronic Device Case, filed Jul. 2, 2013 (London et al.); U.S. patent application Ser. No. 13/947,296 for a System and Method for Selectively Reading Code Symbols, filed Jul. 22, 2013 (Rueblinger et al.); U.S. patent application Ser. No. 13/950,544 for a Code Symbol Reading System Having Adjustable Object Detection, filed Jul. 25, 2013 (Jiang); U.S. patent application Ser. No. 13/961,408 for a Method for Manufacturing Laser Scanners, filed Aug. 7, 2013 (Saber et al.); U.S. patent application Ser. No. 13/973,315 for a Symbol Reading System Having Predictive Diagnostics, filed Aug. 22, 2013 (Nahill et al.); U.S. patent application Ser. No. 13/973,354 for a Pairing Method for Wireless Scanner via RFID, filed Aug. 22, 2013 (Wu et al.); and U.S. patent application Ser. No. 13/974,374 for Authenticating Parcel Consignees with Indicia Decoding Devices, filed Aug. 23, 2013 (Ye et al.).

In the specification and/or figures, typical embodiments and environments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A hand-held device that is capable of self-disinfection, comprising:
    a processor;
    a laser or image sensor for reading symbology;
    a housing that substantially encloses the processor and the laser or image sensor, the housing being at least partially formed of a rigid material that is translucent to light; and
    a ultraviolet light source positioned within the housing for emitting light at a wavelength and an intensity that kills bacteria on the outer surface of the housing's translucent material;
    wherein at least a portion of the ultraviolet light is emitted from the light source orthogonal to the inner surface of the translucent material and through the translucent material to kill bacteria on the outer surface of the translucent material.

2. The hand-held device that is capable of self-disinfection according to claim 1, comprising a power source for powering the ultraviolet light source.

3. The hand-held device that is capable of self-disinfection according to claim 2, wherein the power source is an electrical power source.

4. The hand-held device that is capable of self-disinfection according to claim 1, wherein the ultraviolet light source comprises a light-emitting diode.

5. The hand-held device that is capable of self-disinfection according to claim 1, wherein the ultraviolet light source comprises a plurality of light-emitting diodes arranged in an array.

6. The hand-held device that is capable of self-disinfection according to claim 1, wherein the ultraviolet light is guided to the outer surface of the housing's translucent material.

7. The hand-held device that is capable of self-disinfection according to claim 1, wherein the ultraviolet light is guided through glass to the outer surface of the housing's translucent material.

8. The hand-held device that is capable of self-disinfection according to claim 1, wherein the housing comprises a handle formed of material that is translucent to ultraviolet light.

9. The hand-held device that is capable of self-disinfection according to claim 1, wherein the device is a hand-held computer.

10. The hand-held device that is capable of self-disinfection according to claim 1, wherein the device is a hand-held scanner.

11. A hand-held device that is capable of self-disinfection, comprising:
    a processor, a image sensor for reading code symbology, and a ultraviolet light source positioned within a housing;
    wherein a portion of the housing comprises a rigid material that is translucent to radiation;
    wherein the ultraviolet light source emits ultraviolet light at a wavelength and an intensity that kills bacteria on an outer surface of the housing's translucent material;
    wherein the ultraviolet light emitted from the light source is directed orthogonal to an inner surface of the translucent material and through the translucent material to kill bacteria on the outer surface of the housing's translucent material.

12. The hand-held device according to claim 11, comprising an electrical power source for powering the ultraviolet light source.

13. The hand-held device according to claim 12, wherein the ultraviolet light source comprises a plurality of light-emitting diodes arranged in an array.

14. The hand-held device to claim 13, wherein the ultraviolet light is guided through glass to the outer surface of the housing's translucent material.

15. The hand-held device according to claim 14, wherein the housing's translucent material is present in a location designed to be touched during operation of the device.

16. The hand-held device according to claim 15, wherein the device is a hand-held computer.

17. A hand-held device that is capable of self-disinfection, comprising:

a image sensor for reading symbols;
a processor;
a housing containing the image sensor and the processor, the housing including rigid material that is translucent to light; and
at least one light source positioned within the housing that, when illuminated, emits radiation at a wavelength and an intensity that kills bacteria on an outer surface of the housing's translucent material;
wherein a portion of the radiation emitted from the at least one light source is emitted orthogonal to an inner surface of the translucent material and through the translucent material to kill bacteria on the outer surface of the housing.

18. The device according to claim 17, wherein the light source comprises an ultraviolet light-emitting diode.

19. The device according to claim 18, comprising a power source for powering the light source.

20. The device according to claim 19, wherein the housing's translucent material is present in a location designed to be touched during operation of the device.

\* \* \* \* \*